(12) United States Patent
Molz et al.

(10) Patent No.: US 7,452,130 B2
(45) Date of Patent: Nov. 18, 2008

(54) X-RAY DEVICE WITH AN X-RAY SOURCE FIXED TO A CEILING STAND

(75) Inventors: Claudius Molz, Buckenhof (DE); Peter Scheuering, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 139 days.

(21) Appl. No.: 11/433,684

(22) Filed: May 12, 2006

(65) Prior Publication Data

US 2006/0262906 A1 Nov. 23, 2006

(30) Foreign Application Priority Data

May 13, 2005 (DE) ........................ 10 2005 022 343

(51) Int. Cl.
*H05G 1/10* (2006.01)
*H05G 1/02* (2006.01)
(52) U.S. Cl. ........................ 378/197; 378/101
(58) Field of Classification Search ......... 378/193–198, 378/101
See application file for complete search history.

(56) References Cited

U.S. PATENT DOCUMENTS

| 6,215,846 B1 * | 4/2001 | Mazess et al. ................. 378/62 |
| 6,733,176 B2 * | 5/2004 | Schmitt ....................... 378/196 |
| 6,851,851 B2 * | 2/2005 | Smith et al. .................. 378/189 |
| 6,851,913 B2 * | 2/2005 | Iizuka ......................... 414/626 |
| 6,859,521 B2 * | 2/2005 | Spahn ......................... 378/117 |
| 2005/0189123 A1* | 9/2005 | Richardson et al. ........... 169/46 |

FOREIGN PATENT DOCUMENTS

FR    2699748 A1 *  6/1994

\* cited by examiner

*Primary Examiner*—Edward J Glick
*Assistant Examiner*—Mona M Sanei

(57) ABSTRACT

The invention relates to an x-ray device with an x-ray source fixed to a ceiling stand and a generator connected therewith in order to supply it with power. For simplification purposes, it is proposed in accordance with the invention to provide a conductor rail between the generator and the x-ray source on the ceiling in order to produce an electrical connection, along which conductor rail a ceiling stand accommodating the x-ray source can be moved.

8 Claims, 4 Drawing Sheets

X-RAY DEVICE WITH AN X-RAY SOURCE FIXED TO A CEILING STAND

CROSS REFERENCE TO RELATED APPLICATIONS

This application claims priority to the German Application No. 10 2005 022 343.5, filed May 13, 2005 which is incorporated by reference herein in its entirety.

FIELD OF INVENTION

The invention relates to an x-ray device.

BACKGROUND OF INVENTION

Such an x-ray device is widely known according to the prior art. In such devices, a generator is positioned or mounted on the floor of a room accommodating the x-ray device. An x-ray source is fixed to a ceiling stand which is accommodated, for its part, in a moveable fashion in a guide rail mounted on the ceiling of the room. The x-ray source is connected to the generator via an at least 24 m long high-voltage cable. The high-voltage cable is fixed to the ceiling via a number of fixing means guided on the guide rail in a moveable manner and is suspended between the fixing means in loops. If the position of the x-ray source changes, the high-voltage cable can thus be moved to and fro thereby ensuring an adequate freedom of movement of the x-ray tube.

SUMMARY OF INVENTION

The conventional x-ray device is disadvantageous in many respects. The high-voltage cable suspended from the ceiling in loops can interfere with a positioning of the x-ray source. Aside from this, an injudicious movement of the x-ray tube can even lead to patients or staff sustaining injuries. The provision of the relatively stiff high-voltage cable renders the x-ray source moveable only with a relatively significant amount of effort. The assembly of the high-voltage cable is complex and expensive. Finally, the conventional relatively long high-voltage cable has a capacitance which cannot be ignored, which results in an unwanted current flow and thus x-ray generation even after the generator has been switched off. This in turn undesirably increases the applied dose.

An object of the invention is to eliminate the disadvantages according to the prior art. In particular, an x-ray device is to be specified which can be assembled in the most simple and cost-effective way possible, and which can be operated with a reduced risk of injury. According to a further aim of the invention, the proposed x-ray device is to enable a lowest possible dose to be applied.

This object is achieved by the claims.

Provision is made in accordance with the invention for a conductor rail to be provided on the guide rail and at least one sliding contact interacting with the conductor rail is provided on the ceiling stand so as to produce an electrical connection with the x-ray source. The conductor rail provided according to the invention and the sliding contact interacting therewith allow the conventional long high-voltage cable provided for producing an electrical connection between the generator and the x-ray tube to be dispensed with. The x-ray source can be advantageously moved without any great force. In particular, drives used to assist with a movement of the x-ray facility need not be provided. At the same time, the risk of injury caused with a movement of the x-ray tube by means of the tooing and froing of the high-voltage cable is obviated. The conductor rail can be designed to be comparatively significantly shorter than the conventional high-voltage cable so as to ensure an adequate freedom of movement of the x-ray tube. Consequently, it is possible to reduce an applied dose. Finally, the provision of a conductor rail and a sliding contact interacting therewith enables the x-ray device to be assembled in a simpler manner.

The guide rail can naturally also comprise a number of conductor rails and a number of sliding contacts interacting therewith. In this case, the conductor rails are expediently insulated from one another by an electrically non-conductive material. By way of example, conductor rails arranged next to one another can be separated from one another by a bar made of plastic. In particular, the at least one conductor rail can be accommodated within the guide rail. The sliding contacts can be fixed such that short circuits are avoided. The sliding contacts and the conductor rails are enclosed by a housing-type structure such that contact by operating personnel during the operation of the x-ray facility is impossible.

The proposed combination of a conductor rail and a sliding contact is expediently designed such that it is possible to supply the x-ray tube with currents in the low-voltage, medium-voltage or high-voltage range.

According to an advantageous embodiment, a first transceiver is provided on the guide rail and a second transceiver interacting with the first transceiver is provided on the ceiling stand for the purpose of wireless data transmission. The first and the second transceiver can be transceivers which function optically or by means of radio communication. The data can be transmitted for instance by means of laser pulse signals, infrared transmitters, Bluetooth, wireless LAN connections or suchlike. The transmitted data serves in particular to control and/or regulate as well as monitor the x-ray source.

According to a further particularly advantageous embodiment, the generator comprises means for suspended fixing to a ceiling. If the generator is fixed in a suspended manner, it can be fixed in the vicinity of the guide rail. Once again, the length of the electrical connecting path between the generator and the x-ray source can be shortened. As a consequence, certain capacitative effects can thus be further reduced by means of the length of the conductor.

A further embodiment provides for means for the suspended fixing to be accommodated in a housing. The generator can be included in the housing. The guide rail can extend from the housing. The proposed embodiment is particularly compact and economic in terms of space. A room for accommodating the x-ray device according to the invention can be designed to be smaller than rooms for accommodating conventional x-ray devices.

According to a further particularly advantageous embodiment, the housing is an integral part of the ceiling stand. In this case, the generator 7 can thus be integrated in the ceiling stand. The proposed embodiment is of a particularly compact design. The assembly of the x-ray device can be simplified. In particular, the need to separately fix the generator to the ceiling is dispensed with. Aside from that, only the supply voltage for the generator must be supplied in this case. A conductor guiding the high voltage to be provided for supplying the x-ray source can be designed to be particularly short.

BRIEF DESCRIPTION OF THE DRAWINGS

An exemplary embodiment of the invention is described in more detail below, with reference to the drawings, in which.

DETAILED DESCRIPTION OF INVENTION

Figure 1:
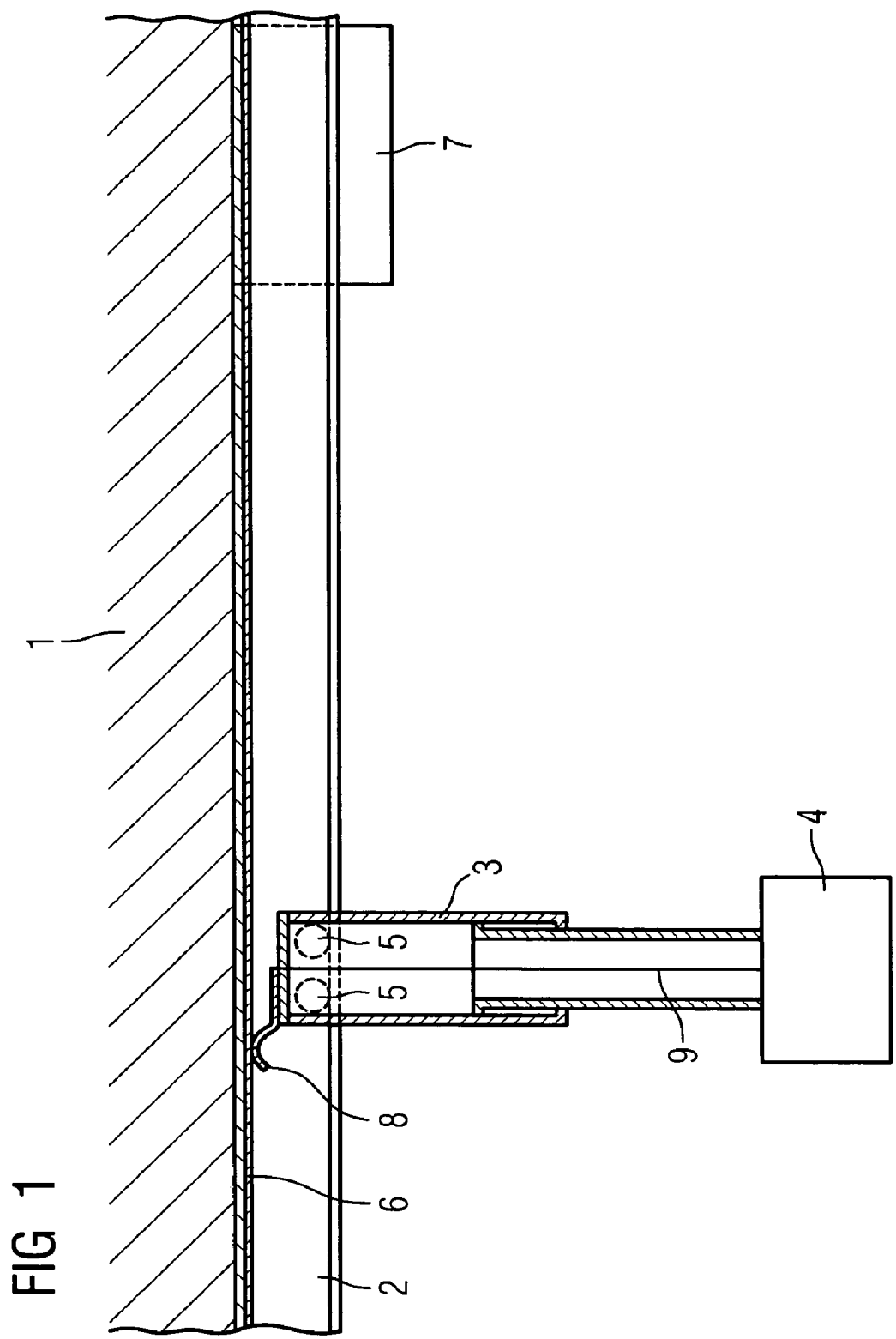
FIG. 1 shows a first schematic sectional view of a device according to the invention.
Figure 2:
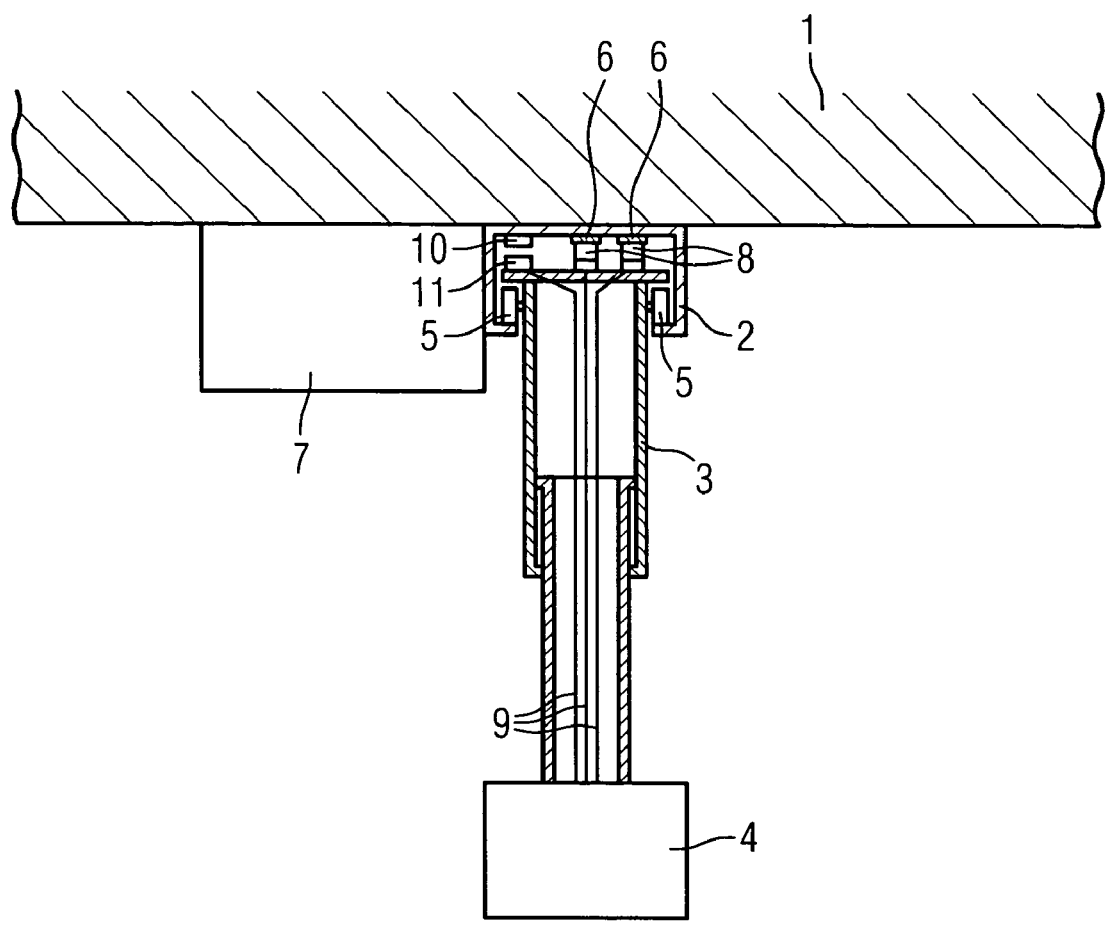
FIG. 2 shows a second schematic sectional view according to FIG. 1.

With the x-ray device shown in FIGS. 1 and 2, a guide rail 2 is fixed to a ceiling 1, along which guide rail a ceiling stand 3 can be moved which is preferably designed to be telescopable. An x-ray source 4, shown here schematically, is fixed to the end of the ceiling stand 3. The guide rail 2 can be designed according to a type of U-profile, with further U-profiles pointing inwards being fixed in turn to the two sides of the U-profile, said further U-profiles serving as tracks for rollers 5 fixed to the ceiling stand 2. Two conductor rails 6, which are connected to a generator 7 in an electrically conductive manner, are fixed to a base plate of the U-profile between the sides of the guide rail 3, preferably interconnecting with an electrically insulating layer (not shown here). Sliding contacts 8 are provided on the ceiling stand 3 corresponding to the conductor rails 6, said sliding contacts 8 being pushed against the conductor rails 6 using a spring-biased force. The sliding contacts 8 are connected to the x-ray source 4 in an electrically conductive manner via a cable 9 for instance. Besides the conductor rails 6, a first transceiver 10 for the wireless transmission of data is further provided on the guide rail 2. A second transceiver 11 corresponding therewith is fixed to the ceiling stand 3 such that a data transmission between the first transceiver 10 and the second transceiver 11 is possible.

Figure 3:
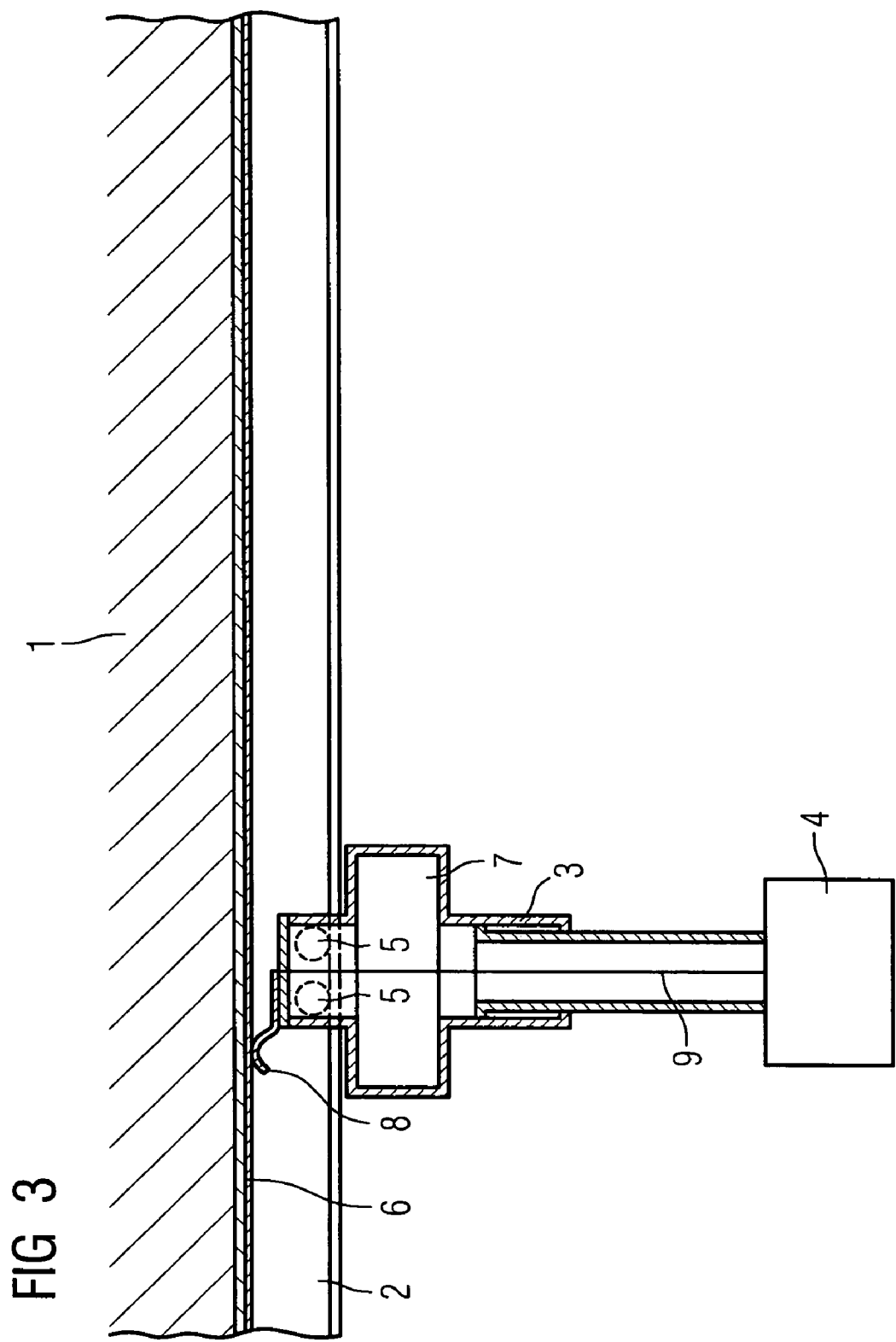
FIG. 3 shows a schematic sectional view of a second embodiment and FIG. 4 shows a second schematic sectional view according to FIG. 3.
Figure 4:
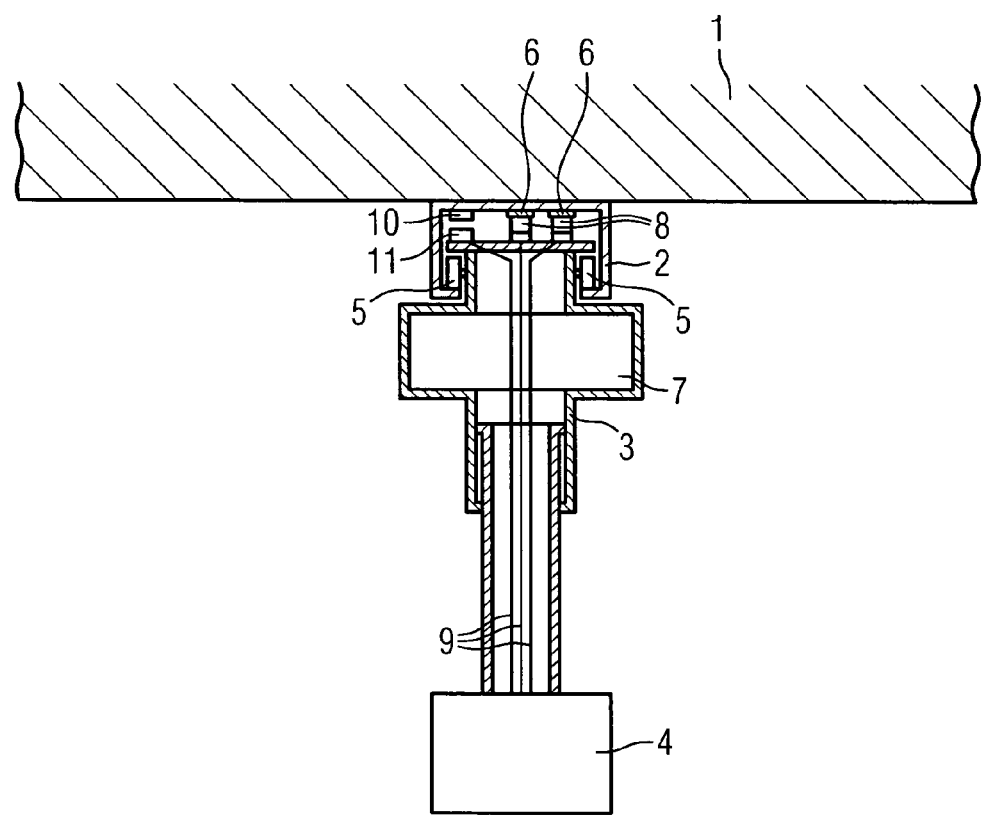

FIGS. 3 and 4 show a second embodiment of the invention. The generator 7 is accommodated here in a ceiling stand 3. To this end, the ceiling stand 3 features a correspondingly suitably designed stand housing in the vicinity of the guide rail 2, which enables the generator 7 to be accommodated. In this case, the generator 7 must only be supplied with a supply voltage required to operate the generator 7 via the conductor rails 6. A high voltage connection from the generator 7 to the x-ray source 5 can be shortened again using this embodiment.

The rollers 5 which are carried in the guide rail 2 serve here as a means of fixing the generator 7 to the ceiling 1.

The invention claimed is:

1. An x-ray device, comprising:
   a guide rail attached to a ceiling;
   at least one conductor rail provided on the guide rail;
   a ceiling stand movable along the guide rail;
   an x-ray source attached to the ceiling stand; and
   a generator suspended from the ceiling and positioned along the conductor rail for supplying power to the x-ray source along the conductor rail, such that at least one sliding contact is fixedly connected to the ceiling stand and in physical contact with the conductor rail for sliding therealong so that as the contact slides along an electrical connection is maintained from the generator through the conductor rail and through the sliding contact to power the x-ray source, wherein separation between the generator and the x-ray source is primarily along the guide rail.

2. The x-ray device according to claim 1, further comprising:
   a first transceiver arranged on the guide rail; and
   a second transceiver communicating with the first transceiver via a wireless data connection.

3. The x-ray device according to claim 2, wherein the first and second transceivers are optical or radio transceivers, 4. The x-ray device according to claim 1, wherein the ceiling stand fixes the generator to the ceiling.

5. The x-ray device according to claim 4, wherein the ceiling stand includes a housing.

6. The x-ray device according to claim 5, wherein the generator is accommodated in the housing.

7. The x-ray device according to claim 5, wherein the housing is an integral part of the ceiling stand.

8. The x-ray device according to claim 5, wherein the housing is permanently fixed to the ceiling, and the guide rail extends from the housing.

* * * * *